(12) United States Patent
Strnad et al.

(10) Patent No.: US 9,649,133 B2
(45) Date of Patent: May 16, 2017

(54) SUPPLEMENTAL FIXATION SCREW

(71) Applicant: Intrepid Orthopedics, Richfield, OH (US)

(72) Inventors: Lee Strnad, Richfield, OH (US); Adam Barlett, Streetsboro, OH (US); Scott Shary, Twinsburg, OH (US)

(73) Assignee: INTREPID ORTHOPEDICS, Richfield, OH (US)

( * ) Notice: Subject to any disclaimer, the term of this patent is extended or adjusted under 35 U.S.C. 154(b) by 0 days.

(21) Appl. No.: 14/938,527

(22) Filed: Nov. 11, 2015

(65) Prior Publication Data

US 2016/0128732 A1    May 12, 2016

Related U.S. Application Data

(60) Provisional application No. 62/078,348, filed on Nov. 11, 2014, provisional application No. 62/078,340, filed on Nov. 11, 2014.

(51) Int. Cl.
*A61B 17/70* (2006.01)
*A61B 17/86* (2006.01)

(52) U.S. Cl.
CPC ...... *A61B 17/7037* (2013.01); *A61B 17/7034* (2013.01); *A61B 17/8685* (2013.01)

(58) Field of Classification Search
CPC ............ A61B 17/7001; A61B 17/7032; A61B 17/7034; A61B 17/7035; A61B 17/7037; A61B 17/7038; A61B 17/704; A61B 17/7041; A61B 17/7046; A61B 17/84; A61B 17/8605; A61B 17/8685
See application file for complete search history.

(56) References Cited

U.S. PATENT DOCUMENTS

| | | | | |
|---|---|---|---|---|
| 5,133,717 A * | 7/1992 | Chopin | ............... | A61B 17/7055 606/264 |
| 5,147,360 A * | 9/1992 | Dubousset | ........... | A61B 17/705 606/250 |
| 5,300,073 A * | 4/1994 | Ray | ..................... | A61B 17/7055 606/250 |
| 5,702,395 A * | 12/1997 | Hopf | ................... | A61B 17/7044 606/250 |
| 5,735,851 A * | 4/1998 | Errico | ................. | A61B 17/7041 606/266 |
| 6,206,879 B1 * | 3/2001 | Marnay | .............. | A61B 17/7035 606/53 |
| 6,520,990 B1 * | 2/2003 | Ray | ..................... | A61B 17/7041 606/264 |
| 6,565,569 B1 * | 5/2003 | Assaker | ............. | A61B 17/7037 606/250 |
| 6,702,817 B2 * | 3/2004 | Beger | ................. | A61B 17/1671 606/294 |
| 6,740,089 B2 * | 5/2004 | Haider | ............... | A61B 17/7032 606/302 |

(Continued)

*Primary Examiner* — Lynnsy Summitt
(74) *Attorney, Agent, or Firm* — Brainspark Associates, LLC

(57) ABSTRACT

Devices, systems and methods for surgical fixation, including multi-screw anchoring devices for anchoring to various anatomical locations such as a sacral level or other anatomy of the spine. Anchoring devices include screw assemblies that are adjustable in a variety of different ways to grant a surgeon various options for placement and/or orientation of the primary and supplemental fixation screws.

20 Claims, 18 Drawing Sheets

(56) References Cited

U.S. PATENT DOCUMENTS

| | | | | |
|---|---|---|---|---|
| 6,749,612 B1* | 6/2004 | Conchy | A61B 17/7044 606/250 |
| 6,964,666 B2* | 11/2005 | Jackson | A61B 17/7035 606/264 |
| 7,063,701 B2* | 6/2006 | Michelson | A61B 17/8605 606/307 |
| 7,842,074 B2* | 11/2010 | Abdou | A61B 17/7067 606/279 |
| 7,892,260 B2* | 2/2011 | Mahoney | A61B 17/7032 606/265 |
| 8,211,151 B2* | 7/2012 | Schwab | A61B 17/7022 606/264 |
| 8,343,199 B2* | 1/2013 | Tyber | A61B 17/1717 606/281 |
| 8,361,130 B2* | 1/2013 | Daly | A61B 17/7032 606/304 |
| 8,591,513 B2* | 11/2013 | Overes | A61B 17/68 606/319 |
| 9,017,329 B2* | 4/2015 | Tyber | A61B 17/1717 411/457 |
| 9,044,282 B2* | 6/2015 | Tyber | A61B 17/1717 |
| 9,060,808 B2* | 6/2015 | Overes | A61B 17/68 |
| 9,084,646 B2* | 7/2015 | Sevrain | A61B 17/86 |
| 9,149,316 B2* | 10/2015 | Appenzeller | A61B 17/864 |
| 2004/0111088 A1* | 6/2004 | Picetti | A61B 17/7001 606/265 |
| 2004/0162558 A1* | 8/2004 | Hegde | A61B 17/7044 606/287 |
| 2010/0160978 A1* | 6/2010 | Carbone | A61B 17/866 606/305 |
| 2010/0174320 A1* | 7/2010 | Truckai | A61B 17/70 606/279 |
| 2010/0274296 A1* | 10/2010 | Appenzeller | A61B 17/8605 606/305 |
| 2011/0184470 A1* | 7/2011 | Gorek | A61B 17/7011 606/279 |
| 2011/0230884 A1* | 9/2011 | Mantzaris | A61B 17/1717 606/64 |
| 2011/0230920 A1* | 9/2011 | Gorek | A61B 17/7001 606/305 |
| 2011/0282398 A1* | 11/2011 | Overes | A61B 17/861 606/304 |
| 2013/0085534 A1* | 4/2013 | Hainard | A61B 17/7055 606/278 |
| 2014/0018858 A1* | 1/2014 | Laeng | A61B 17/7002 606/270 |
| 2014/0058457 A1* | 2/2014 | Appenzeller | A61B 17/864 606/304 |
| 2014/0200618 A1* | 7/2014 | Donner | A61B 17/1757 606/281 |
| 2014/0277154 A1* | 9/2014 | Perry | A61B 17/7044 606/270 |
| 2016/0106477 A1* | 4/2016 | Hynes | A61B 17/7044 606/279 |
| 2016/0106479 A1* | 4/2016 | Hynes | A61B 17/7059 606/286 |
| 2016/0128732 A1* | 5/2016 | Strnad | A61B 17/7037 606/279 |

* cited by examiner

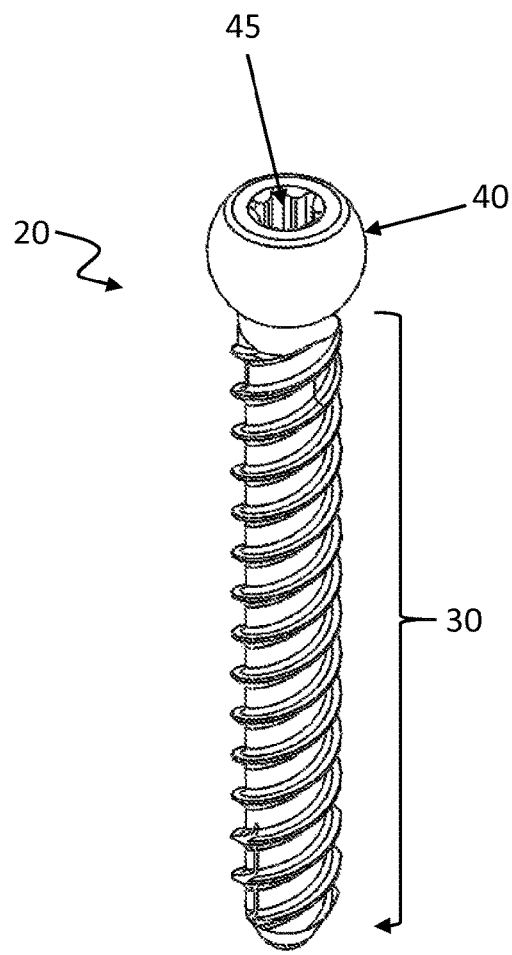
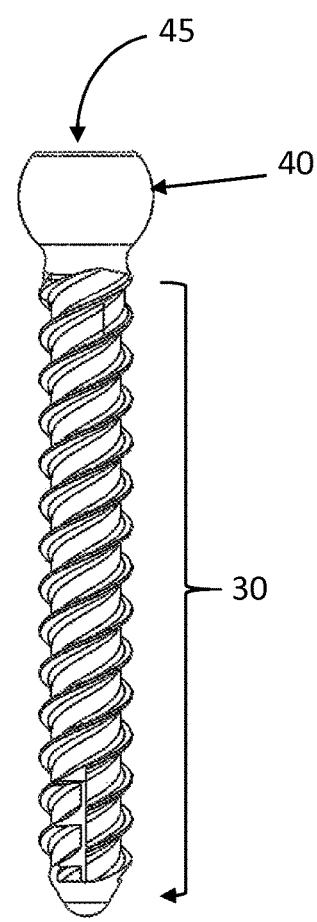
FIG. 4A
FIG. 4B

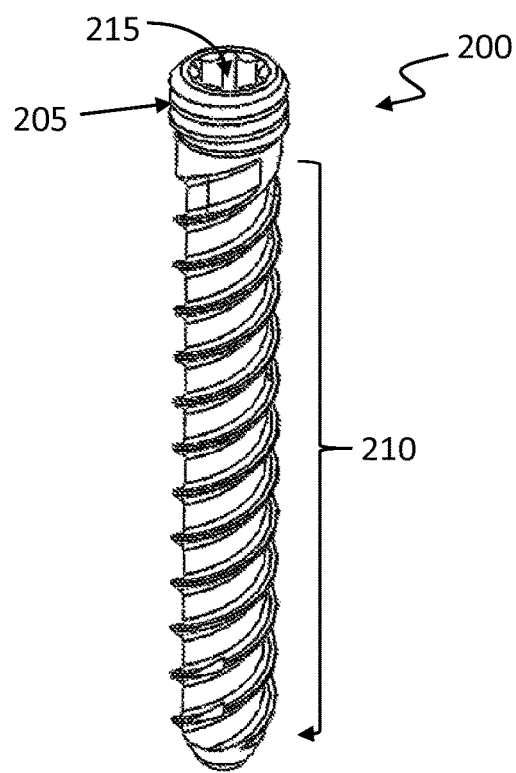
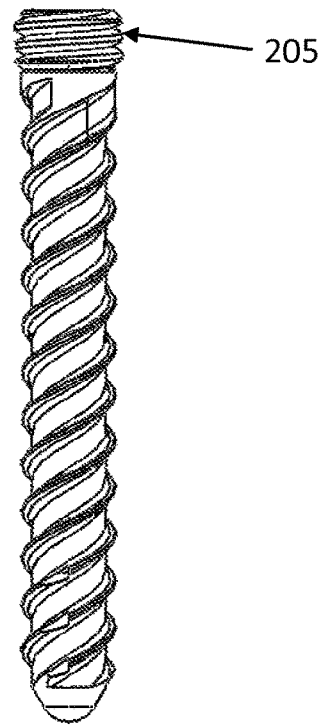
FIG. 7A  FIG. 7B
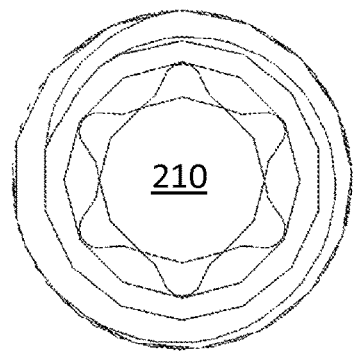
FIG. 7C

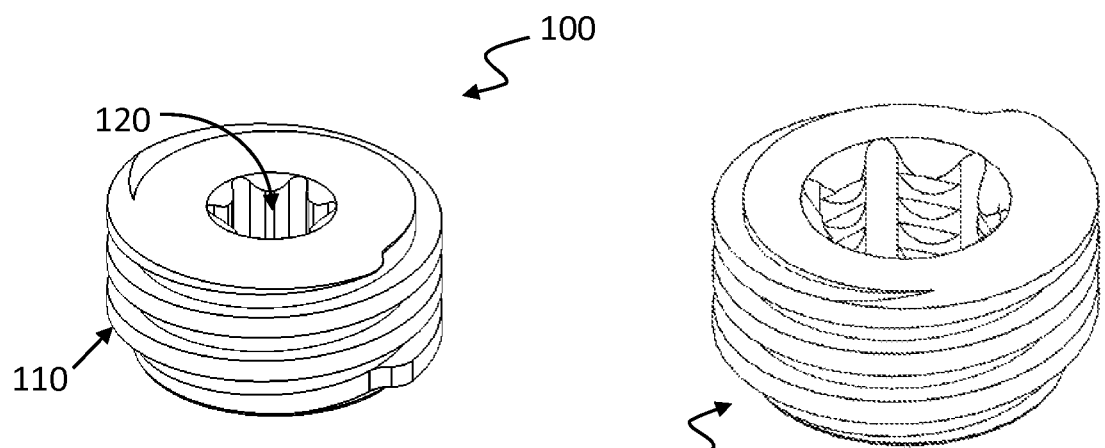
FIG. 8A
FIG. 8B
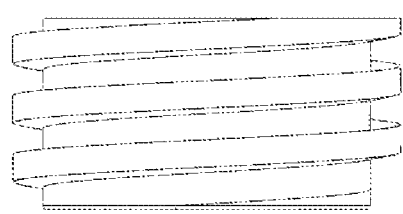
FIG. 8C
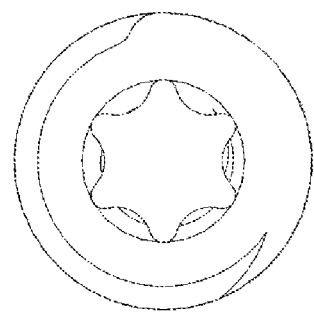
FIG. 8D
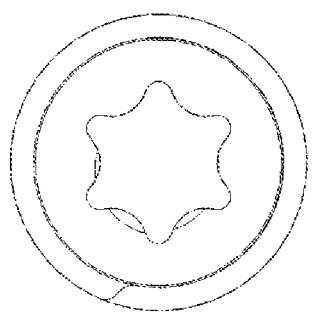
FIG. 8E

SUPPLEMENTAL FIXATION SCREW

CROSS-REFERENCE TO RELATED APPLICATIONS

This application claims the benefit of U.S. Provisional Patent Application Ser. No. 62/078,348 entitled "Supplemental Fixation Screw," filed Nov. 11, 2014, and U.S. Provisional Patent Application Ser. No. 62/078,340 entitled "Threaded Setscrew Crosslink," filed Nov. 11, 2014, the disclosures of which are incorporated by reference herein in their entireties.

TECHNICAL FIELD

The present invention relates to the field of surgery, and more specifically to devices for connecting to bones of the spine and sacrum for maintaining bones or other anatomical structures in a fixed and/or spaced apart relationship, including in conjunction with the use of bone alignment rods and bone screws.

BACKGROUND OF THE INVENTION

A wide variety of instrumentation systems and surgical techniques have been developed to stabilize and correct spinal conditions and/or deformities, including systems and techniques for correcting degenerative disc disease, spondylolisthesis, spinal deformities, or other spinal conditions through minimally invasive or invasive spinal surgery. In many cases, spinal surgery may include a desire to stabilize a portion of the spine to allow bone or other tissue growth between vertebral bodies, such that a portion of the spine is stabilized or "fused" into a solitary unit and/or specified shape. Commonly known as spinal fusion, this type of stabilization is a commonly-accepted surgical procedure which promotes fusing or growing together of two or more vertebrae in the spine.

The spine is a series of individual bones called vertebrae, separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no significant side-to-side curve, it does have a series of front-to-back curves, giving it a gentle "S" shape. The spine curves in at the lumbar region, back out at the thoracic region, and back in at the cervical region.

One type of spinal fusion procedure is a posterior spinal fusion surgery. This procedure is performed posteriorly, or from the back of the patient, as opposed to anteriorly, or through the abdomen. There are many surgical fusion procedures performed with pedicle screw fixation, which can include (among others) posterolateral gutter fusion surgery, posterior lumbar interbody fusion ("PLIF") surgery and transforaminal lumbar interbody fusion ("TLIF") surgery.

Moreover, there are many approaches and systems for performing posterior spinal surgery. Various exemplary systems can include titanium construction that are compatible with current CT and MRI scanning technology, low profile implant systems, top-loading and top-tightening systems, and other parameters. Some systems also include cross-connectors that allow an implant to be applied across a dual-rod construct for additional strength and stabilization.

A wide variety of popular systems for spinal stabilization and/or fusion employ the use of pedicle or other type screws and rods, in which screw assemblies can be secured into the bony structures of the patient's vertebrae, and one or more rods or other devices are connected between the screw assemblies, typically disposed longitudinally along the length of the spinal segment to anchor vertebral bodies relative to each other. The rods can assume a wide variety of shapes (i.e., straight, curved or irregularly shaped), various positions (i.e., posterior, anterior and/or lateral) and/or configurations (including the use of cross-arms or cross-connectors, where desired) according to the patient's anatomy and/or the correction desired. In many cases, the patient's anatomy and/or the desired surgical correction may require aligning one or more rods and associated anchoring screws at numerous different angles and/or orientations along the length of the portion of the treated spinal segment.

A unique challenge for bony fixation can arise when the lower levels of the spine are involved, as loosening or breakage of pedicle screws in the lower levels of the spine is not infrequent. Pull out and breakage of pedicle screws typically results in failure of the stabilization system. In such a case, as the stabilization is lost, many of the original complaints from the patient return (i.e., pain and numbness of the low back and leg, inability to walk, foot weakness). In addition, the patient may feel pain at the implantation area due to the loose implant.

Where pedicle screws are implanted into the sacral levels of the spine, loosening or breakage of the pedicle screws is often seen in the first sacral vertebra. There are various reasons why pedicle screws suffer a higher than normal rate of failure at the sacral level. Primarily, the sacral screw bears more load than all the other screws in a typical spinal construct, because the S1 vertebra is the point where the lumbar spine and the sacrum intersect. When a lumbosacral stabilization is performed, the majority of the pull-out forces from the screws in the upper vertebral levels are transmitted to the sacrum, which typically acts as a single-piece unit. Consequently, a properly selected and implanted sacral screw should be very strong. But anatomical constraints can often limit the size and permitted anchoring approaches for sacral screws, rendering the S1 pedicle screw fixation weaker than equivalent lumbar pedicle screws. For example, the anterior-posterior diameter of the S1 body is generally shorter than lumbar vertebrae, requiring a shorter screw than compared to the lumbar pedicle screws. Concurrently, if the anatomy allows a longer S1 screw, it is often required to direct the screw medially to the midline, which can be difficult due to regional anatomical constraints and the presence of the iliac bone. The iliac bone can prevent the screw head from being tilted laterally and cause the screw to be placed straight, and can force the surgeon to create a longer skin incision, make a larger lateral soft tissue retraction and/or even require resection of some of the ilium to properly position the screw.

Because the placement of classical pedicle screws at the sacral level is technically difficult and can often increase surgical trauma experienced by the patient, specialized sacral plates and screws have been developed to utilize additional screw fixation to augment the primary anchoring screw. However, many of these devices require an expansion of the surgical field and/or preparation for implantation of a new screw to be performed (i.e., preparation of a new entry point, fluoroscopy, etc.), and it may become necessary to extend the spinal rod for fastening of the rod to the new screw. Moreover, many of these existing sacral fixation systems are rather large and bulky, and the limited modularity and/or flexibility of the components in many of these systems can render the systems difficult for a surgeon to use effectively.

SUMMARY OF THE INVENTION

One aspect of the present invention includes a recognition of a need for a spinal fixation system that facilitates the use of a supplemental fixation screw and that incorporates features and components that can easily accommodate a wide range of patient anatomical variability. Various embodiments described herein are directed to spinal fixation systems, and more particularly to multi-screw anchoring devices for anchoring to a sacral level or other anatomy of the spine. In many embodiments, an object of the present invention is to provide a sacral screw assembly which is adjustable in a variety of different ways to give the surgeon options for placement and orientation of the primary and supplemental fixation screws.

Various of the embodiments described herein relate to devices for connecting a plurality of screws to an underlying bony anatomy to desirably increase fixation strength and torsional rigidity, with the device further being useful in conjunction with a variety of other spinal system components. The adjustability and variability in the device allows it to be easily attached to a targeted primary anatomical region using a primary fixation screw, and then portions of the device can be manipulated to allow a secondary fixation screw of the device to be fixated into a targeted secondary anatomical region, even where there is a significant amount of anatomical variation that creates widely divergent screw placement.

The embodiments disclosed herein include a housing having a high degree of strength and incorporate extremely strong connections to the various screws fixated into the bony anatomy.

Further features and advantages of the invention, as well as structures and operation of various embodiments of the invention, are further elaborated in detail below with references to the accompanying drawings

BRIEF DESCRIPTION OF THE DRAWINGS

The present invention should be better understood in conjunction with the detailed description below and the accompanying drawings. In the drawings, like reference numbers typically indicate identical, similar and/or functionally similar elements.

FIGS. 4A and 4B depict perspective and side view of an exemplary primary fixation screw;

FIGS. 7A through 7C depict various views of an exemplary supplemental fixation screw which incorporates various features of the present invention;

FIG. 8A depicts a perspective views of an exemplary set screw;

FIGS. 8B through 8E depict various views of an alternative embodiment of a threaded set screw which incorporates various features of the present invention;

DETAILED DESCRIPTION OF THE DISCLOSURE

Figure 1:
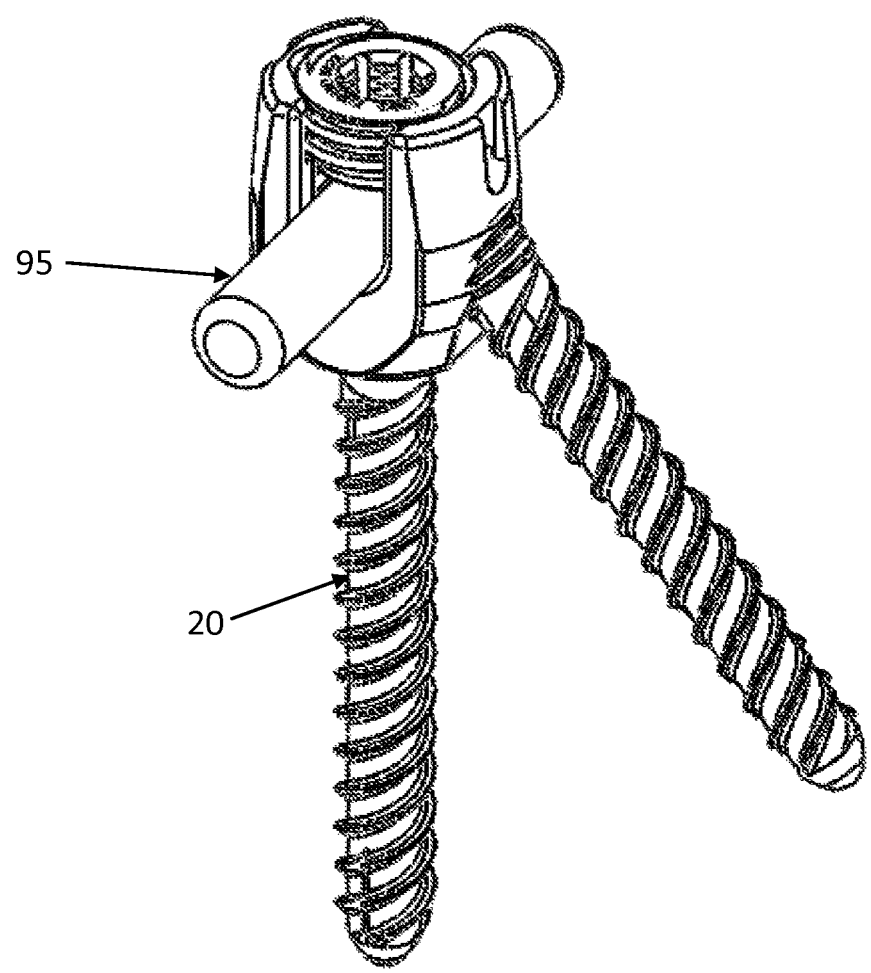
FIG. 1 depicts a perspective view of one embodiment of a supplemental screw fixation construct with an associated fixation rod, incorporating various features of the present invention.
Figure 2A:
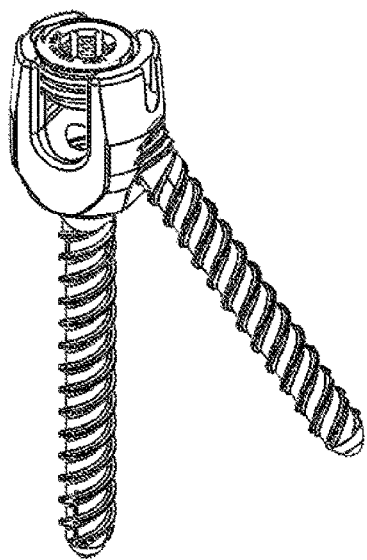
FIGS. 2A and 2B depict a side perspective and cross-sectional views, respectively, of the supplemental screw fixation construct of FIG. 1.
Figure 2B:
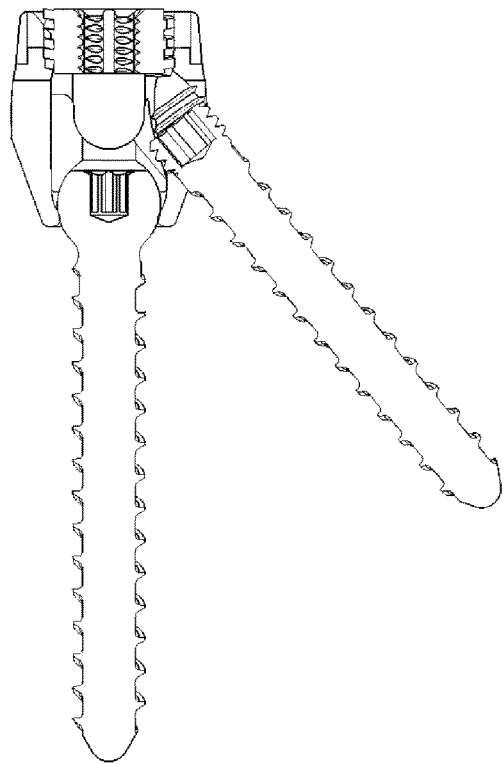

In the following detailed description, for purposes of explanation, numerous specific details are set forth to provide a thorough understanding of the various embodiments of the disclosure. Those of ordinary skill in the art will realize that these various embodiments are illustrative only and are not intended to be limiting in any way. In addition, for clarity purposes, not all of the routine features of the embodiments described herein may be shown or described for every alternative embodiment. One of ordinary skill in the art would readily appreciate that in the development of any such actual implementation, numerous implementation-specific decisions may be required to achieve specific design objectives. These design objectives may vary from one implementation to another and from one developer to another, and the variations thereof are contemplated and included in the present disclosure.

Various of the embodiments described herein include features that facilitate the use and/or modification of surgical constructs, including surgical spinal fusion and/or motion stabilization constructs, which allow the surgeon the ability to accommodate a wide variety of anatomical variation and/or desired surgical correction, yet allows secure fixation of the relevant anatomy when in a tightened or "fixed" condition. In addition, various embodiments described herein facilitate the surgeon's assembly, disassembly and/or adjustment of one or more components intra-operatively.

It should be understood that the term "system," when referring to various embodiment described in the present invention, can refer to a set of components which includes multiple bone stabilization components such as superior, cephalad or rostral (towards the head) components configured for implantation into a superior vertebra of a vertebral motion segment and inferior or caudal (towards the feet) components configured for implantation into an inferior vertebra of a vertebral motion segment. A pair of such component sets may include one set of components configured for implantation into and for stabilization of the left side of a vertebral segment and another set configured for the implantation into and for stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system can also involve stacking of component sets in which each set includes a superior component, an inferior component, and one or more medial components there between, which may be interconnected and/or independent from each other.

Various of the components described herein, when operatively implanted, may be engaged or interface with each other in a manner that enables the treated spinal motion segment to mimic the function and movement of a healthy segment, may alter the relative movement of the various spinal structures in a desired manner and/or may simply fuse the segments such as to eliminate pain and/or promote or enhance healing. The interconnecting or interfacing systems can include one or more structures or members that enable, limit and/or otherwise selectively control spinal or other body motion. The structures may perform such functions by exerting various forces on the system components, and by extension on the target vertebrae. The manner of coupling, interfacing, engagement or interconnection between the subject system components may involve compression, distraction, rotation or torsion, or various combinations thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

A spinal stabilization system may be installed in a patient to stabilize a portion of a spine, which can include systems that immobilize and/or fixate a specific portion of the spine, as well as systems that control or limit spinal motion to varying degrees (i.e., dynamic stabilization and/or motion limiters). Spinal stabilization may be used, but is not limited to use, in patients having degenerative disc disease, spinal stenosis, spondylolisthesis, degenerative lumbosacral joint, neuromuscular scoliosis, pelvic obliquity, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

Spinal fixation devices such as those described herein can be utilized to facilitate anchoring of spinal components to sacral levels of the spine in fusion procedures, desirably in conjunction with supplemental fixation to surrounding anatomical features, such as the ala portion of the sacrum, as well as a variety of other surgical uses. Moreover, various features of the present invention could be employed with equal utility in anatomical locations other than sacral levels that might benefit from the various supplemental fixation systems described herein, such as other levels of the spine as well as other anatomical locations outside of the spine.

Components

In various exemplary embodiments, a spinal fusion system (or other orthopedic construct, including spinal motion and/or dynamic stabilization constructs) may contain various combinations, sizes and configurations of the various components described hereafter. In an associated exemplary surgical method for implanting a spinal stabilization system, the patient may be placed in a prone position on a surgical table, which for a partially-open and/or minimally-invasive procedure may include a radiolucent table with clearance available for a C-arm of a fluoroscope (i.e., a Jackson table with a radiolucent Wilson frame attachment may be used).

Figure 3:
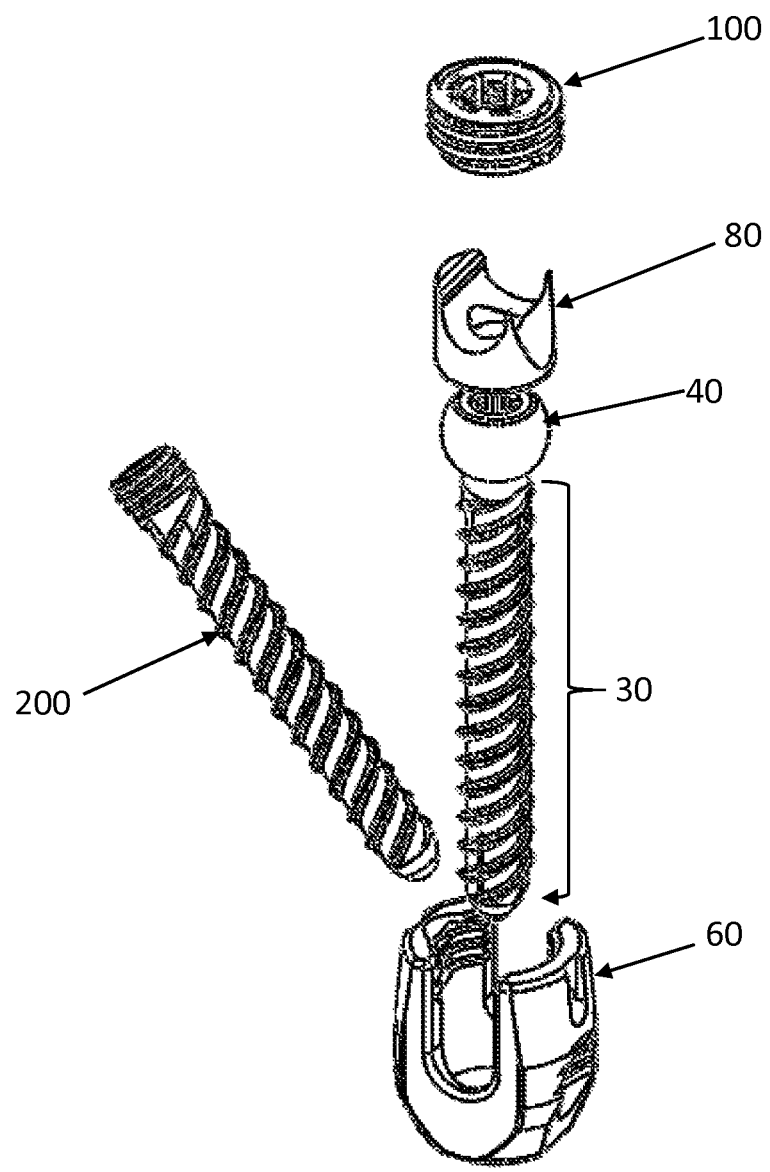
FIG. 3 depicts an exploded view of the supplemental screw fixation construct of FIG. 2A.
Figure 5A:
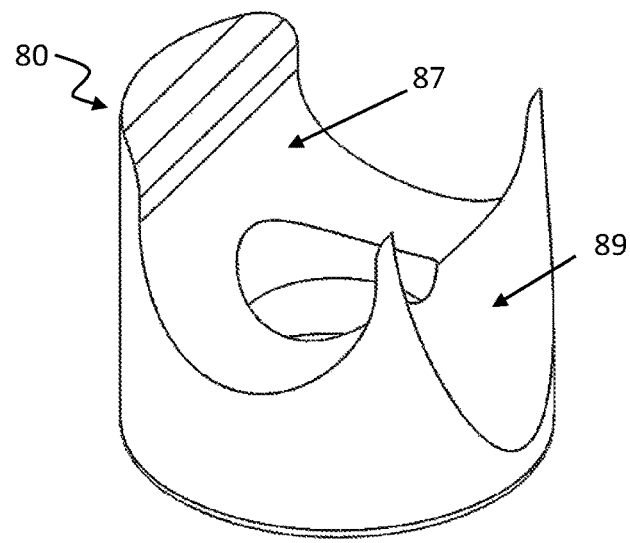
FIGS. 5A through 5G depict various views of an exemplary insert which incorporates various features of the present invention.
Figure 5B:
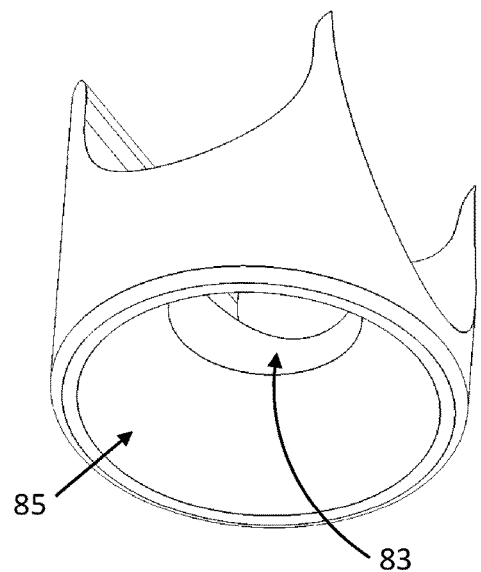
Figure 5C:
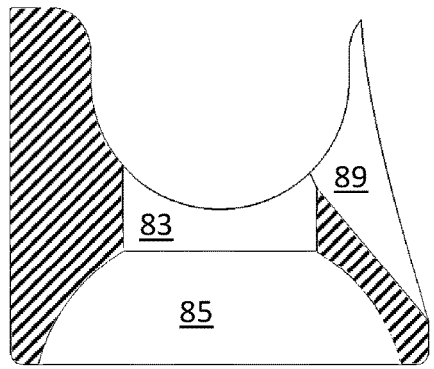
Figure 5D:
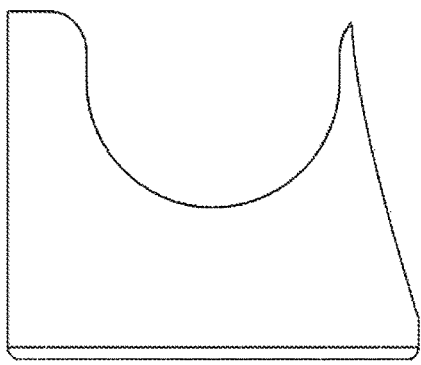
Figure 5E:
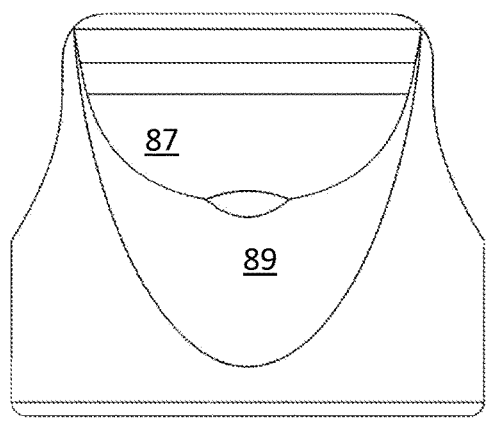
Figure 5F:
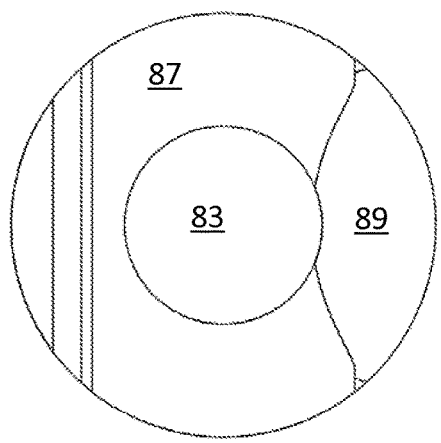
Figure 5G:
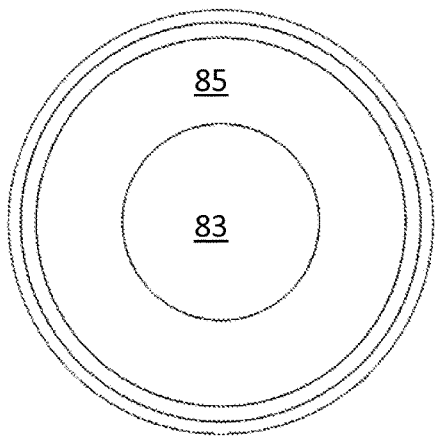
Figure 6A:
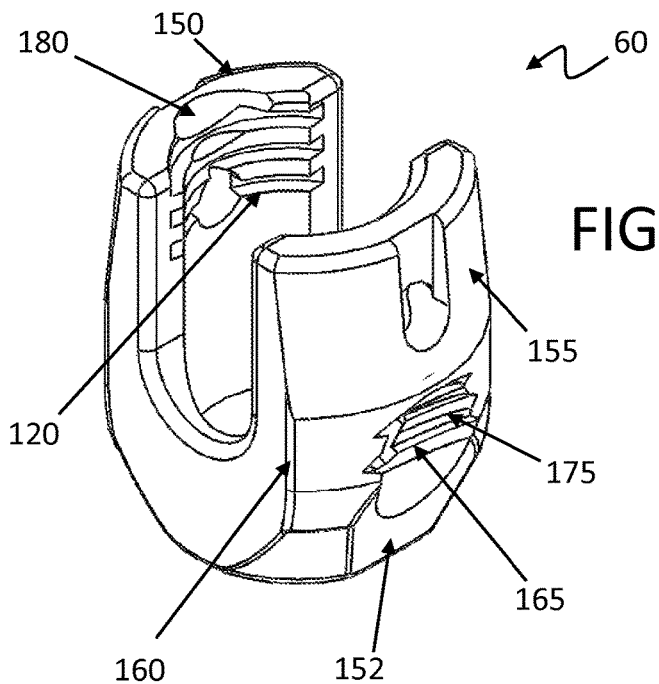
FIGS. 6A through 6H depict various views of an exemplary tulip head which incorporates various features of the present invention.
Figure 6B:
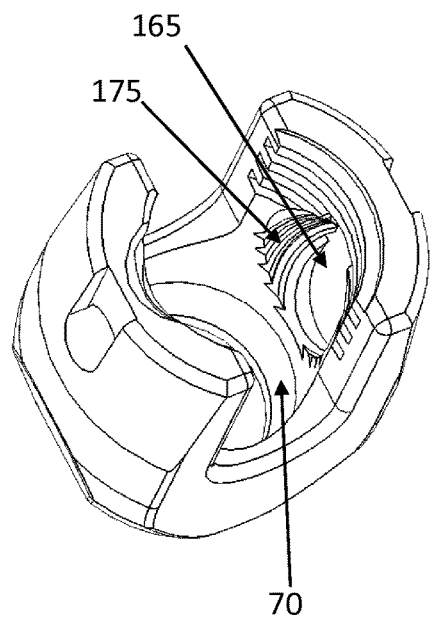
Figure 6C:
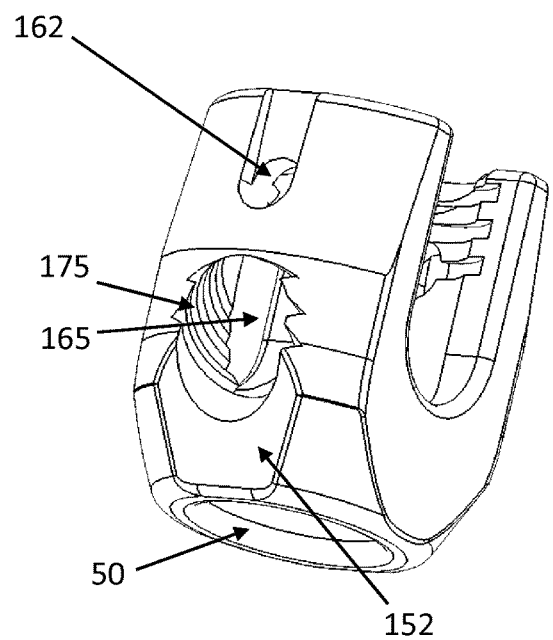
Figure 6D:
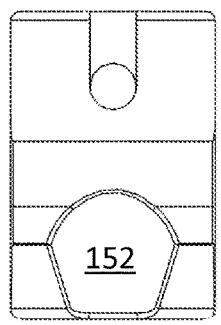
Figure 6E:
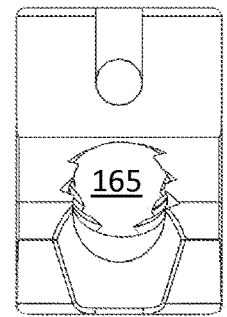
Figure 6F:
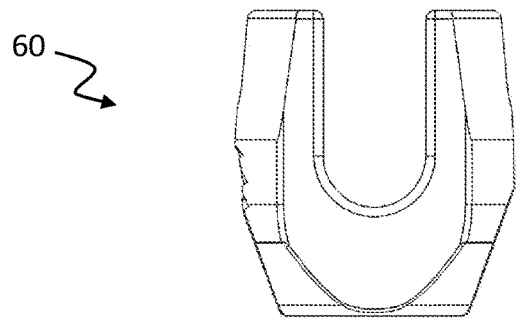
Figure 6G:
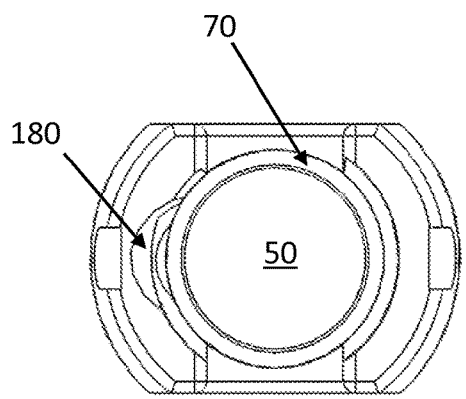
Figure 6H:
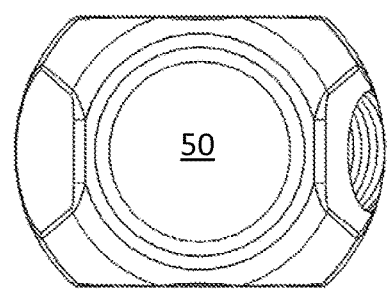

FIG. 1 depicts a front perspective view of one embodiment of a supplemental screw fixation construct 10 in an exemplary "fully implanted" configuration, incorporating various features of the present invention. In this embodiment, the construct 10 includes a primary fixation or sacral screw 20, which can be similar to a pedicle screw and is typically used for securement to bony anatomy (not shown) in a known manner. As can be best seen from FIGS. 3, 4A and 4B, the sacral screw 20 can include a screw shank 30 and a rounded screw head 40, with the screw shank 30 desirably sized and configured to pass through a lower opening 50 (see FIG. 6C) in a tulip head connector 60 in a known manner. The adjustability between the rounded screw head 40 and a curved inner surface 70 of the lower opening 50 desirably provides for polyaxial adjustability of the shank 30 relative to the tulip head 60 in a known arrangement. While polyaxial adjustment is described in this embodiment, it should be understood that other types of screws and/or other attachment devices (i.e., spinal hooks, wire cages, etc.) could be utilized in conjunction with various features of the disclosed invention, including the use of monoaxially adjustable and/or fixed screw shank and connecting tulip head designs.

The supplemental screw fixation construct 10 can further include an insert 80 (see FIGS. 3 and 5A through 5G) which desirably fits within the tulip head 60, the insert having a lower insert surface 85 which interacts with and engages the screw head 40. The insert 80 can also have a curved upper surface 87, which engages with a fixation rod 95 or other feature. The insert 80 can also include a scalloped or cutaway section 89, which desirably facilitates placement of a secondary fixation screw 200 through the tulip head 60, which in the disclosed embodiment can be an alar screw or other bone-engaging screw that significantly strengthens the anchoring of the device into the bone. The angle on the scalloped or cutaway section can be virtually any angle, including between 30 to 60 degrees, and as shown in the disclosed embodiment is approximately 50 degrees.

The insert 80 can further include a central opening or bore 83, which desirably provides the surgeon with access through the insert to the hexalobe or other type socket 45 in the rounded head 40 of the sacral screw using a surgical driving instrument.

FIGS. 6A through 6H depict various views of one embodiment of a tulip head 60, incorporating various features of the present invention. The tulip head 60 can include a body 160 having a first arm 150 and a second arm 155 that define a slot and/or channel there between, the slot being sized for receiving a support rod 95. As previously noted, the tulip head 60 includes a lower opening 50 to receive the shank portion of the bone screw, and a curved inner surface 70 of the lower opening 50 which engages with the rounded screw head 40 and provides for polyaxial adjustability of the shank 30 relative to the tulip head 60. If desired, one or more chamfered surfaces 152 can be provided on an outer surface of the tulip head, to allow for greater clearance and/or angulation between the tulip head and the surrounding anatomy. One or more holes or notches 162 can be provided on the external surfaces of the tulip head for engagement with various surgical manipulation tools (not shown).

The tulip head 60 further includes at least one side opening 165 in the side of the body 160 and/or arm 155, the opening 165 being sized and configured to accept a secondary fixation screw, which in this embodiment can be an alar fixation screw 200. Desirably, the side opening is formed at an approximately 45 degree angle from a vertical or longitudinal axis of the housing, although holes with other angles could be utilized in alternative embodiments, including 60 degree holes, 55 degree holes, 50 degree holes, 40 degree holes, 35 degree holes, 30 degree holes and/or other angles (which could be measured from the vertical and/or longitudinal axis of the housing or measured from an axis transverse to the housing axis). In the disclosed embodiment, a small amount of material can be removed from an inner surface of the opposing arm 150 to create a scalloped portion 180, which desirably provides additional clearance for the alar screw 200 when it is advanced from the inside of the tulip head and through the side opening 165. Depending upon the angle of the side opening, this scalloped portion 180 can extend deeper and/or shallower into the arm 150, and in certain embodiments may not be necessary. Desirably, the scalloped portion 180 will be designed such that the housing 60 will retain sufficient threads on the inner portion of the arm 150 to facilitate engagement with the locking screw 100. In the disclosed embodiment, the scalloped portion is formed at an approximately 50 degree angle from the vertical axis of the tulip head.

An inner surface of the side opening 165 will desirably include a threaded portion 175 for engaging with a corresponding upper threaded section 205 of the alar screw 200. Desirably, the side opening 165 will be sized and configured to permit the lower threaded portion 210 of the alar screw 200 to freely pass through the opening 165, but the threaded portion 175 will desirably engage with the corresponding upper threaded section 205 to secure the alar screw 200 within the tulip head 60 as it is rotated within the opening 165. In the disclosed embodiment, the threaded alar screw will desirably engage at least 2 threads with the surrounding threaded opening, although various other construct designs and/or thread forms may desirably engage more and/or fewer threads.

If desired, the threads of the threaded portion 175 may not extend the full length of the opening, such that the alar screw 200 may be unable to be fully threaded through and exit the opening 165. For example, the threaded section may extend from an inner section of the tulip head to just short of the outer surface of the tulip head, such that rotation of the alar screw within the threaded portion 175 eventually rotates the threads of the upper threaded section into contact with the unthreaded portion of the opening 165, desirably blocking further rotation of the alar screw and potentially "locking" the alar screw into a final desired position. Desirably, this final position could include where the head of the alar screw is fully set within the housing such that the rod can fully seat against the insert without significantly contacting the alar head, or where such contact is minimal. If desired, the rod and other components of the system could be arranged such that the rod contacts and/or is in close proximity to the alar screw such that, in the event of loosening of the alar screw, the position and presence of the rod would prevent "backout" of the alar screw.

In another alternative embodiment, a tapered thread could be employed which "locks" the alar screw in a desired location after sufficient thread engagement is obtained. In another alternative embodiment, the upper threaded section 205 of the alar screw 200 could include an unthreaded portion (not shown) at its proximal end (i.e., adjacent to the hexalobe socket 215), with this unthreaded section preventing further rotation of the alar screw through the opening 165 when a desired position for the alar screw 200 is reached. In various alternative embodiments, the opening 165 could include a variety of other features to engage with the alar screw, which could include taper locks, friction fits, and/or expansion/compression features incorporated into the screw and/or opening, with various amounts of motion and/or micro-motion permitted and/or acceptable between the alar screw and the housing.

In the disclosed embodiment, the cutaway section 89 of the insert 80 will desirably align with the opening 165 of the tulip head 60, so as to allow the alar screw 200 to be advanced into the opening 165 without significant interference. If desired, the tulip head 60 can include a retaining feature (not shown) that retains and holds the insert within the tulip head in a desired position and/or orientation. Exemplary retaining features to prevent such undesired rotation and/or displacement of the insert could include a pin, flat or swage.

While the opening in the disclosed embodiment is depicted aligned generally transverse to a longitudinal axis of the rod, other angulations for the side opening (relative to the rod axis) could be utilized, if desired. In addition, the slot or channel in the tulip head 60 could be sized to allow some small amount of "play" or movement of the rod within the slot (prior to tightening of the set screw), if desired.

FIGS. 7A through 7C depict various views of a supplemental fixation screw, which in this embodiment is depicted as an alar fixation screw 200. The alar screw 200 includes an upper threaded section 205 and a lower threaded portion 210, which in this embodiment incorporates machine-type threads in the upper section and bony anatomy-engaging threads in the lower portion (i.e., cortical and/or cancellous bone engaging threads, for example). A hexalobe socket 215 is desirably formed in the upper threaded section 205, which can be engaged with a corresponding surgical driver for advancement of the alar screw through the opening 165 and into the desired bony anatomy of the patient. If desired, the surgical driver for the alar screw could comprise a standard hex-driver screwdriver, or could comprise a specialized surgical tool that is used for other components of the construct.

Desirably, the hexalobe sockets described in conjunction with various components herein can be the same size as other hexalobe sockets of the system (to reduce the number of driving tools required for the procedure), or different socket sizes can be incorporated as desired. In addition, it should be understood that, while a hexalobe shape is depicted in the figure, those skilled in the art should appreciate that the hexalobe configuration described herein, along with the various corresponding surgical tools, could be formed in various alternative shapes, such as a hexagonal socket, a square, a slot, a cross, an oval or other shapes. Similarly, the employment of other size drivers, with various size sockets formed in the various corresponding components, is contemplated herein. In various alternative embodiments, various screws or other components could alternatively incorporate friction fits, taper fits and/or camming features for securement, if desired.

In one exemplary embodiment, the alar screw 200 depicted herein can include machine-type threads that desirably mate with corresponding machine-type threads formed in the opening 165, thereby creating a substantially rigid connection between the housing and the supplemental screw and significantly increasing the strength and rigidity of the fixation construct in a desired manner. While double lead machine threads are depicted (which can desirably allow rotation of the alar screw to advance the screw equivalent distances along both the machine and bone-engaging threads), it should be understood that a wide variety of thread forms known in the art could be utilized for either or both of the machine and bone-engaging threads. In various embodiments, threaded surfaces could comprise square or "acme-type" threads, although the use of a wide variety of thread forms known in the art for any of the threads and/or threaded components described herein is contemplated herein, including the use of flat threads, negative angle threads and/or saw-tooth threads, such as threads having a 10 degree or other back angle.

In various additional embodiments, various semi-rigid and/or non-rigid fixation connections could be provided between the supplemental fixation screw and the housing, including the use of monoaxial and/or polyaxial type connections between the housing and the supplemental screw. Similarly, it is contemplated that the supplemental fixation screw could include an adjustable connection (i.e., monoaxial and/or polyaxial) while the primary fixation screw (i.e., the sacral screw) could incorporate a fixed and/or threaded connection (i.e., such as reversing the screw/housing connection methods as described herein), if desired.

FIG. 8A depicts one exemplary embodiment of a set screw 100 for use in securing the rod 95 into the tulip head 60 and "locking" polyaxial movement of the tulip head relative to the primary fixation screw 20. Desirably, once a fixation rod is positioned within the curved upper surface of the insert, an externally threaded surface of the set screw can be threaded into corresponding internal threads in the tulip head 60, and tightened such that a lower surface of the set screw 100 contacts the rod, which in turn compresses the insert against the screw head in a known manner and can "lock" or otherwise immobilize the movement of the screw shank relative to the tulip head, as well as to securing the pedicle screw construct and rod together in a known manner. In the disclosed embodiment, the threaded set screw will desirably engage at least 3 threads with the surround tulip head, although various other construct designs and/or thread forms may desirably engage more and/or fewer threads. In one exemplary embodiment, the externally threaded surface can include a sawtooth or other-type thread form having a back angle of approximately 10 degrees, with a corresponding thread form in the interior of the tulip head, which desirably reduces and/or obviates "splay" of the tulip head during tightening of the threaded set screw (although various other thread form shapes and/or dimensions could be utilized for any of the screw threads described herein, as is well known in the art).

The set screw desirably includes an interior bore 120 (which in this embodiment is centrally located, although non-centrally located bores are also contemplated herein) which can extend partially and/or fully through the set screw. The interior bore in this embodiment includes recessed wall sections forming a generally hexalobe shape (which could include the formation of a socket arrangement commonly referred to as a TORX™ socket, commercially available from Camcar Textron of Providence, R.I., USA), which desirably accommodates a hexalobe wrench or other surgical tool for insertion, removal, tightening and/or loosening of the threaded set screw from the tulip head. In the disclosed embodiment, the various screws can desirably be tightened using a standard hexalobe-25 screwdriver, with the employment of counter-torque wrenches, as well known in the art, for such tightening actions, if desired.

FIGS. 8B through 8E depict various views of an alternative embodiment of a threaded set screw 100A, which could be utilized in combination with the various components and features described herein as well as those relative to the threaded set screw. Various features and aspects of the threaded set screw and related crosslink components are disclosed in copending U.S. Provisional Patent Application Ser. No. 62/078,340 entitled "Threaded Setscrew Crosslink," the disclosure of which is hereby incorporated herein by reference in its entirety.

Figure 9A:
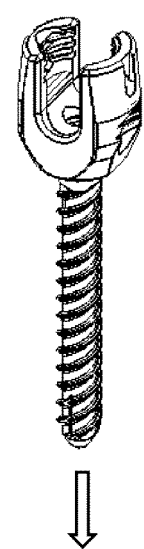
FIGS. 9A through 9E depict exemplary steps of implanting the supplemental screw fixation construct of FIG. 1.
Figure 9B:
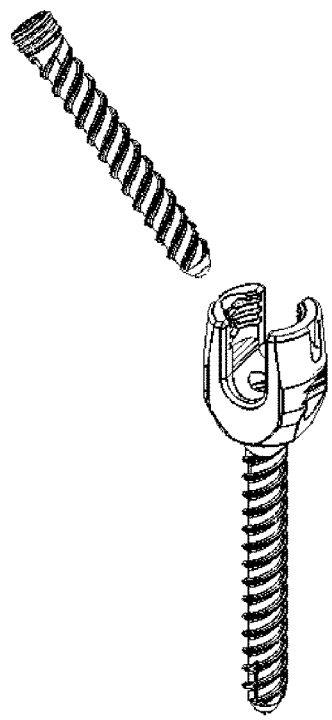
Figure 9C:
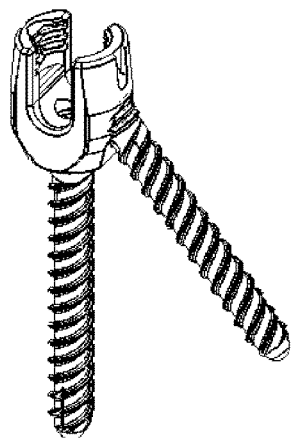
Figure 9D:
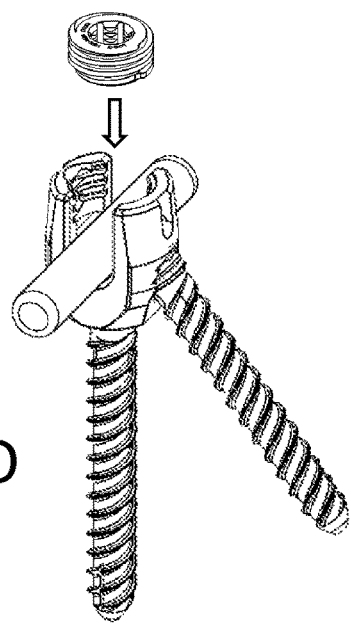
Figure 9E:
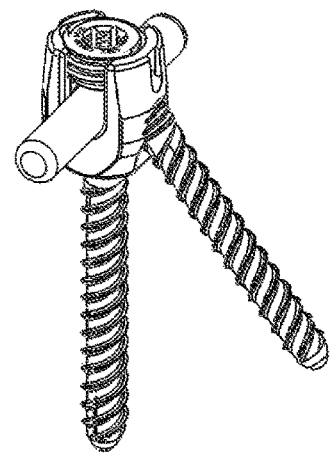

In use, a surgeon can initially place the sacral screw and assembled insert and tulip head construct into a targeted spinal anatomy of the patient in a known manner, including the use of various preparation and placement tools known in the art for placement of pedicle screws. Desirably, a driving tool (not shown) can extend through the opening in the insert, with its tip extending into the hexalobe socket of the sacral screw, and the sacral screw advanced into the bone by the surgeon (see FIG. 9A). The driving tool can then be removed, which desirably allows the tulip head to be freely rotatable relative to the sacral screw, which in the disclosed embodiment allows for polyaxial movement of the tulip head. The surgeon can then realign and/or freely rotate the tulip head such that the side opening 165 is realigned towards a desired anatomical location for the supplemental fixation screw, and this supplemental anatomy can be prepared (i.e., by drilling and/or broaching, if desired) for the supplemental screw. Once the supplemental anatomy has been prepared, a supplemental fixation screw (which in this embodiment comprises an alar screw 200) can be introduced through the side opening 165 (see FIG. 9B) and secured to the supplemental anatomy, with rotation of the alar screw also desirably securing the alar screw into the corresponding threads of the side opening 165 as previously described (see FIG. 9C). Once this desired screw fixation is accomplished, a fixation rod can be placed into the slot and the set screw 100 tightened into the tulip head (see FIG. 9D), thereby locking and immobilizing the construct in a desired manner (see FIG. 9E).

A wide variety of screw sizes, lengths and/or shapes can be provided for the various primary and supplemental fixation components, but in many cases the primary fixation screw will be somewhat larger than the supplemental fixation screw. For example, a sacral screw of between 5 to 8 mm may be provided that desirably anchors the construct and provides the majority of fixation forces, with a supplemental fixation alar screw of 5 mm or less in diameter. The alar screw desirably can bear some portion of the loading experienced by the construct, and desirably will take some of the force off of the sacral screw and aid in keeping the system in a fixed position. The alar screw can also be useful in counteracting torque forces acting on the sacral screw, and/or will desirably withstand various bending forces on the alar screw under normal loading conditions.

In the various embodiments, screws can be desirably secured in their respective final positions by application of a relatively higher torque force to "lock" the screw in a final position in a known manner, with the employment of counter-torque wrenches for such tightening actions, if desired. However, in various alternative embodiments a locking or camming mechanism could be incorporate into one or all of the screws and/or receiver designs, which could include features to desirably prevent "backing out" of the screw under unusual loading conditions, if desired.

The various features of the disclosed supplemental screw fixation construct represent a significant improvement over preexisting systems in terms of flexibility, versatility, compactness and strength. The present design allows for two or more fixation screws to be accommodated in the same housing, and provides for a fully rigid connection between the housing and at least one of the fixation screws, yet accommodates patients having significant anatomical variability. Moreover, the inclusion of supplemental fixation screws of varying shapes and/or sizes in a kit form (which may include a plurality of sacral screws of differing shapes or sizes, with or without pre-attached tulip heads) can provide the surgeon with the ability to arrange the various components as the surgeon desires. In one exemplary embodiment, a kit including a preassembled sacral screw, insert and tulip head construct can be provided, with one or more set screws, and the kit can further include a plurality of alar screws having a 5 mm diameter and differing lengths of 35, 40 and 45 mm.

Figure 10A:
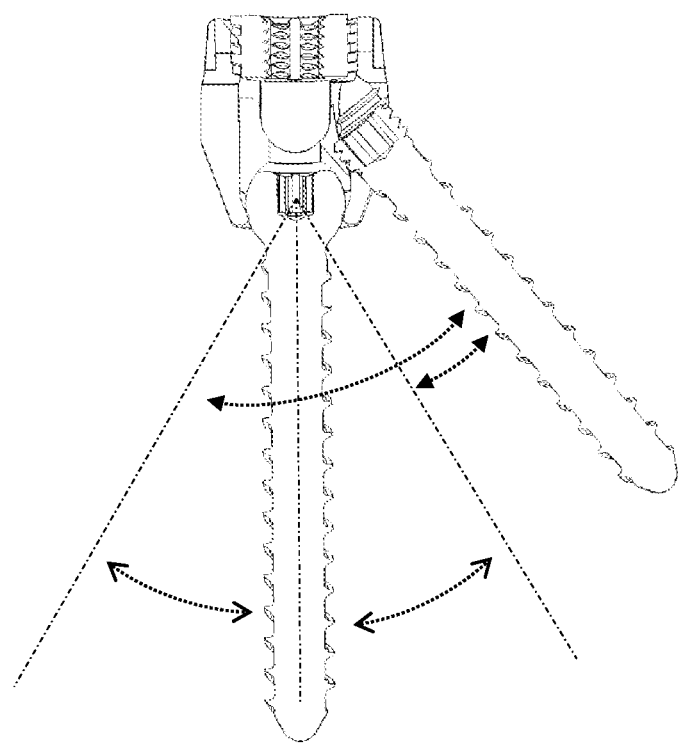
FIGS. 10A through 10C depict various views of component variability and/or adjustability.
Figure 10B:
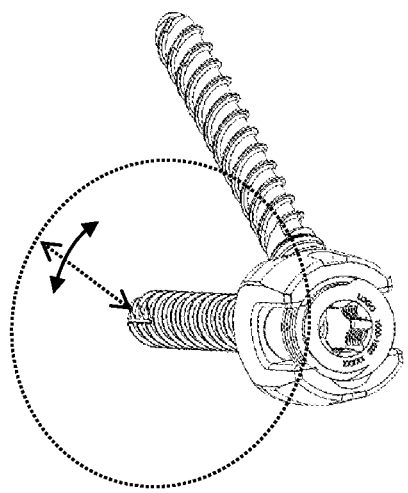
Figure 10C:
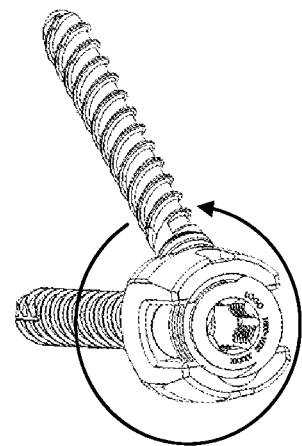

In the disclosed embodiment, the various components desirably do not significantly increase the posterior profile of the system as compared to pre-existing designs, and the amount of anatomical "real estate" required for fixation of the disclosed components can be significantly less than required by currently available plating and/or sacral screw systems. Another significant advantage over the prior art relates to the simplified connecting and/or fixating mechanisms for the various components described herein as compared to more complex clamping and/or locking mechanisms of the prior art. Moreover, the polyaxial adjustability and free rotation between the sacral screw shank and the tulip head (see FIGS. 10A through 10C) allows a surgeon to adapt the construct to a wide variety of alignments and/or configurations, as well as potentially help avoid healthy bone, nerves, vasculature and/or other tissues. In addition, the disclosed components can be implanted via a less-invasive and/or minimally-invasive fashion, including through a single incision for placement of both the sacral and alar screws.

Because the disclosed fixation systems are compatible with standard rods, they can be used as a part of a standard pedicular screw fixation construct. The use of two or more screws interlocked by a single tulip head can provide considerably higher resistance against pull-out, torque and/or failure of fixation as compared to currently available systems. In addition, no additional entry point for the bone is needed, as the entry point of a single screw can be used. Moreover, placing the primary fixation screw can be easily accomplished, and the supplemental screw can be placed without extending the skin incision, increase muscle retraction and/or remove any iliac bone or other anatomical structures. By using the primary screw positioning as a guide for the supplemental screw, the supplemental screw(s) can be placed securely and with little additional effort.

In another exemplary embodiment, a surgical kit can be provided that provides a plurality of screws of differing lengths, diameters, shapes, sizes and/or configurations for use in accommodating various surgical corrections in a variety of anatomical situations. If desired, the supplemental fixation screw and/or the sacral fixation screw could include similar or differing features, by incorporating screws of different characteristics, a wide range of construct characteristics can be achieved with a limited catalog of part sizes. For example, a surgical kit could include one or more sacral screws having a diameter of between 5 to 8 millimeters (with varying lengths of 35 to 60 mm—in 5 mm increments), supplied with one or more alar screws of different lengths having a diameter of approximately 5 mm.

Figure 11A:
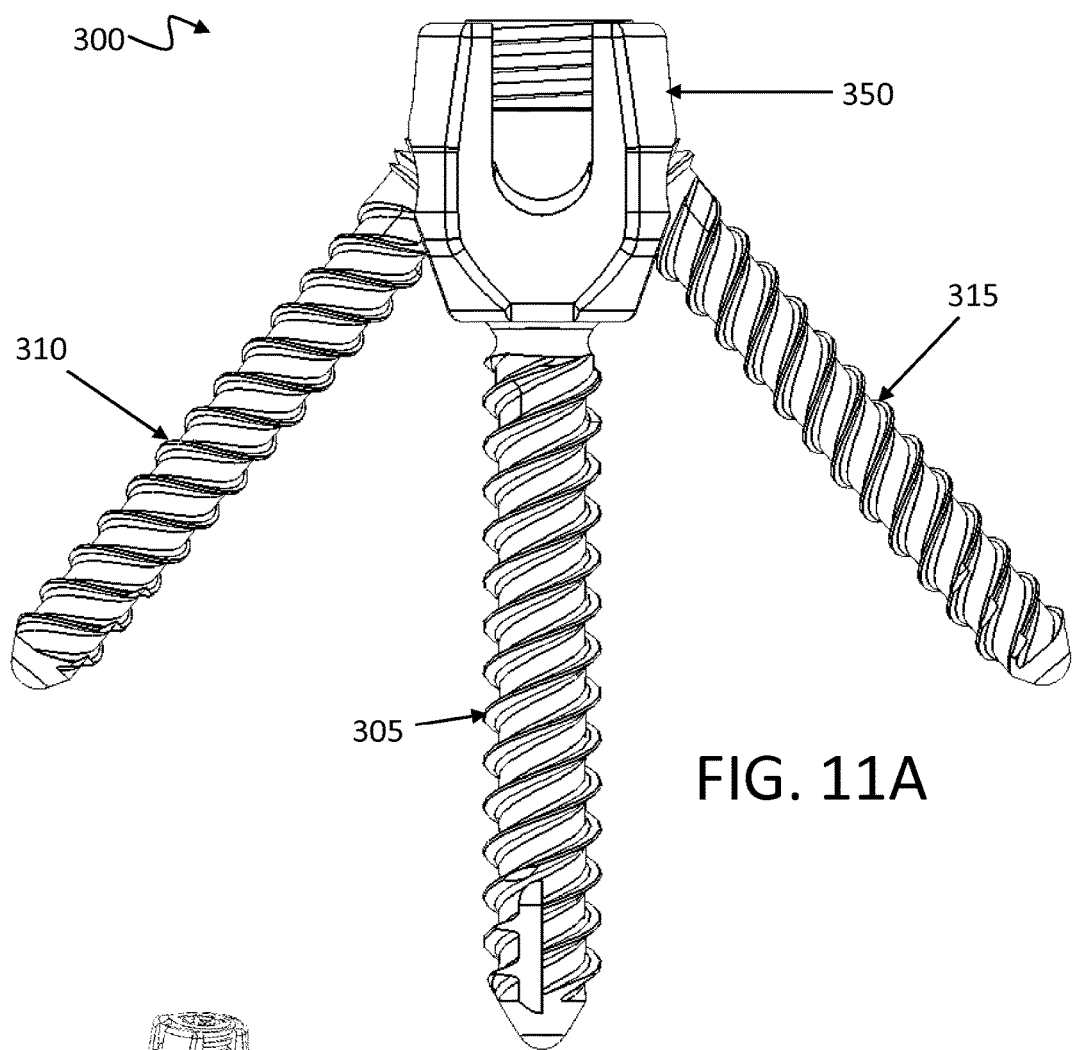
FIGS. 11A through 11C depicts various views of another alternative embodiment of a supplemental screw fixation construct with a plurality of associated fixation screws, incorporating various features of the present invention.
Figure 11B:
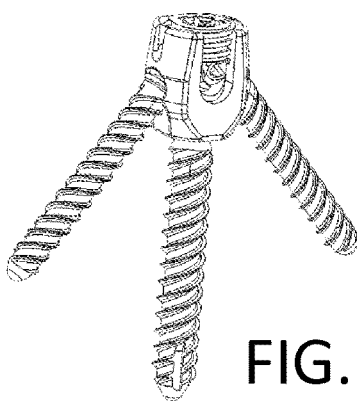
Figure 11C:
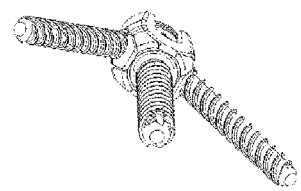

FIGS. 11A through 11C depict another exemplary embodiment of a supplemental screw fixation construct 300 comprising a primary fixation screw 305 and a plurality of supplemental fixation screws 310 and 315. In this embodiment, each of the supplemental screws extend outward from a respective supplemental opening, which in this embodiment are formed in opposing medial and lateral portions of the tulip head 350. If desired, a surgeon could use either or both of the supplemental openings to accommodate fixation screws or other fixation devices.

Figure 12:
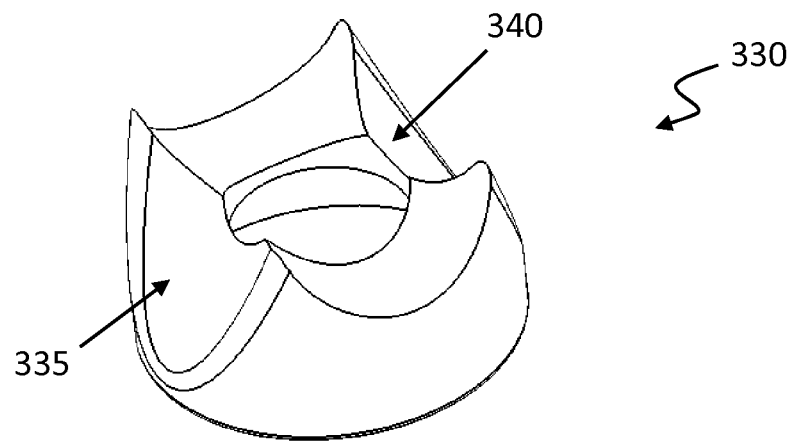
FIG. 12 depicts a perspective view of an alternative insert for the supplemental screw fixation construct of FIG. 11A.
Figure 13:
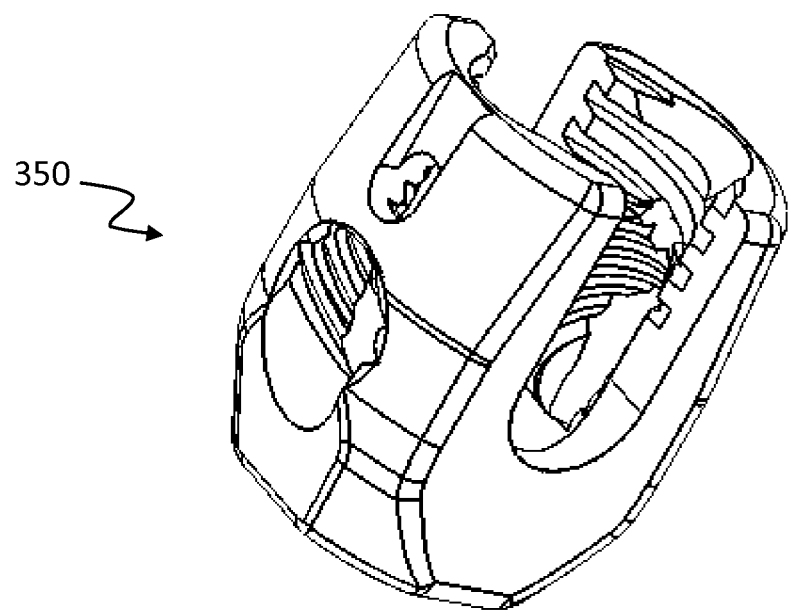
FIG. 13 depicts a perspective view of an alternative tulip head for the supplemental screw fixation construct of FIG. 11A.

FIG. 12 depicts a perspective view of an insert 330 suitable for placement within a tulip head 350 (see FIG. 13) of the construct 300 of FIGS. 11A through 11C. In this embodiment, the insert 330 desirably includes a plurality of cut-away or scalloped regions 335 and 340, to desirably accommodate the supplemental fixation screws extending through one or both of the supplemental openings in the tulip head. The angle on the scalloped or cutaway section can be virtually any angle, including between 30 to 60 degrees, and as shown in the disclosed embodiment is approximately 50 degrees.

In one additional embodiment of a supplemental screw fixation construct, each of the opposing supplemental openings could incorporate a different angulation, allowing a surgeon to select the appropriate opening for the desired supplemental fixation. For example, if a screw fixation construct incorporated a first supplemental opening having an angulation of 35 degrees on a first side of the tulip head, and a second supplemental opening having an angulation of 45 degrees on the opposing side of the tulip head, then the surgeon could simply rotate the tulip head to the appropriate supplemental angulation for the surgical procedure (i.e., where the ala anatomy might approximate 30 degrees in some patients, and 45 degrees in others). If desired, the remaining fixation hole could be unused, or the hole could be filled with a threaded plug or similar device (which could form part of the surgical kit, if desired).

Figure 14A:
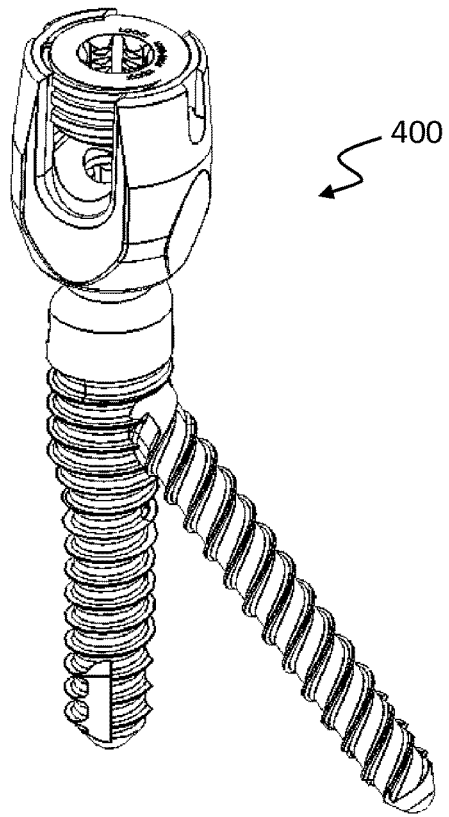
FIGS. 14A and 14B depicts perspective views of another alternative embodiment of a supplemental screw fixation construct incorporating various features of the present invention.
Figure 14B:
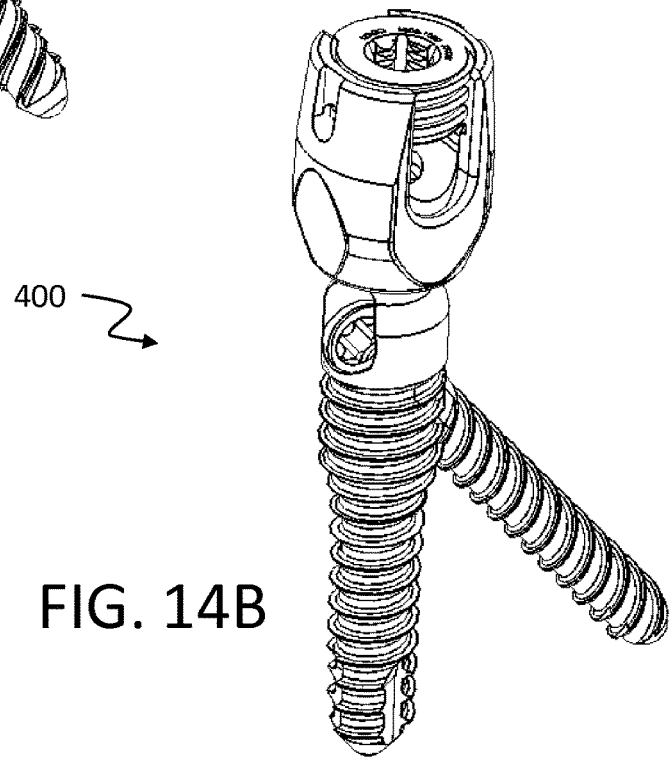
Figure 15A:
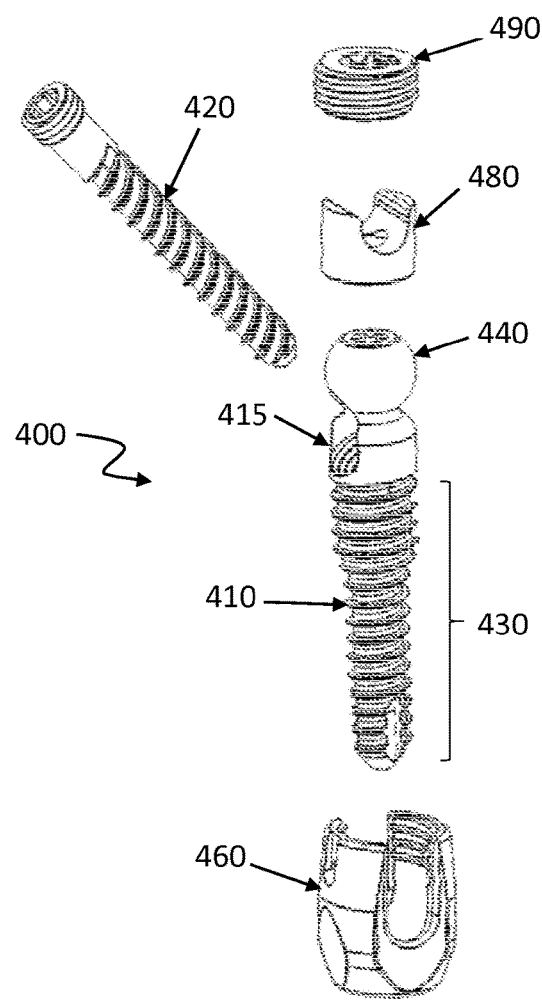
FIGS. 15A and 15B depict exploded perspective views of the supplemental screw fixation construct of FIG. 14A.
Figure 15B:
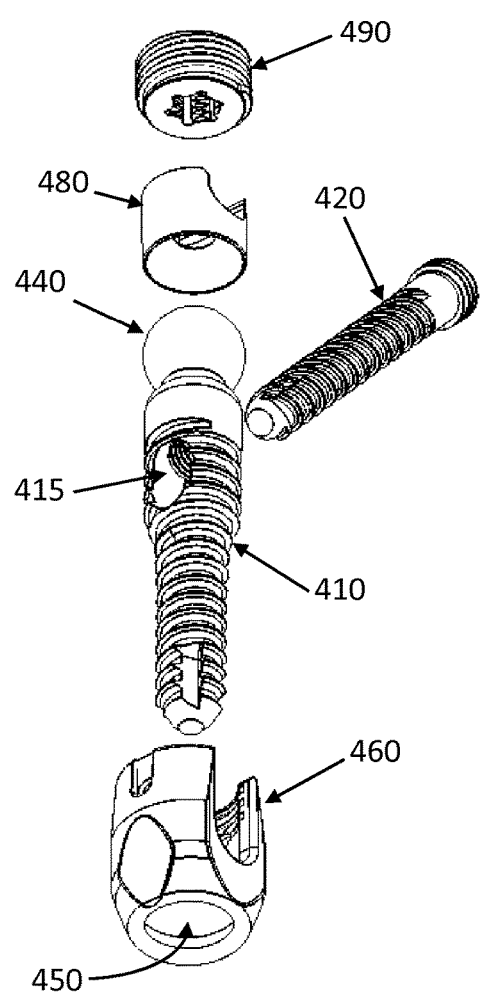

FIGS. 14A and 14B depict front and rear perspective views of another additional embodiment of a supplemental screw fixation construct 400, incorporating various features of the present invention. In this embodiment, the construct 400 includes a primary fixation screw 410 having a screw opening 415 for accommodating a supplemental fixation screw 420 (see FIGS. 15A and 15B). The primary fixation screw 410 can include a screw shank 430 and a rounded screw head 440 with the screw shank 430 desirably sized and configured to pass through a lower opening 450 (see FIG. 15B) in a tulip head connector 460. The adjustability between the rounded screw head 440 and a curved inner surface of the lower opening 450 desirably provides for polyaxial adjustability of the shank 430 relative to the tulip head 460. While polyaxial adjustment is described in this embodiment, it should be understood that other types of screws and/or other attachment devices (i.e., spinal hooks, wire cages, etc.) could be utilized in conjunction with various features of the disclosed invention, including the use of monoaxially adjustable and/or fixed screw shank and connecting tulip head designs.

The supplemental screw fixation construct 400 can further include an insert 480 which desirably fits within the tulip head 460, the insert having a lower insert surface which interacts with and engages the screw head 440. The insert 480 can also have a curved upper surface, which engages with a fixation rod (not shown) or other feature. The construct 400 will also desirably include a set screw 490 for use in securing the fixation rod into the tulip head 460 and "locking" polyaxial movement of the tulip head 460 relative to the primary fixation screw 410. If desired, the set screw 490 could be a standard set screw, or the set screw 490 could comprise an internally threaded set screw, such as described and depicted in FIGS. 8B through 8E.

FIGS. 16A through 16E depict various views of one exemplary embodiment of a primary fixation screw 410. The primary fixation screw 410 includes a screw shank 430 having a distal shank section 432 and a proximal shank section 434, with the distal shank section shown as having a smaller diameter than a corresponding diameter of the proximal shank section 434. In various alternative embodiments, the distal shank section may include a diameter that is the same as and/or approximates the proximal shank section diameter, with a supplemental fixation screw having a smaller diameter than the primary fixation screw, if desired. Moreover, in various alternative embodiments a transition section between the distal and proximal shank sections could be gradual, smooth and/or abrupt, with a straight and/or curved transition, if desired.

Figures 16A, 16B, 16C, 16D, 16E:
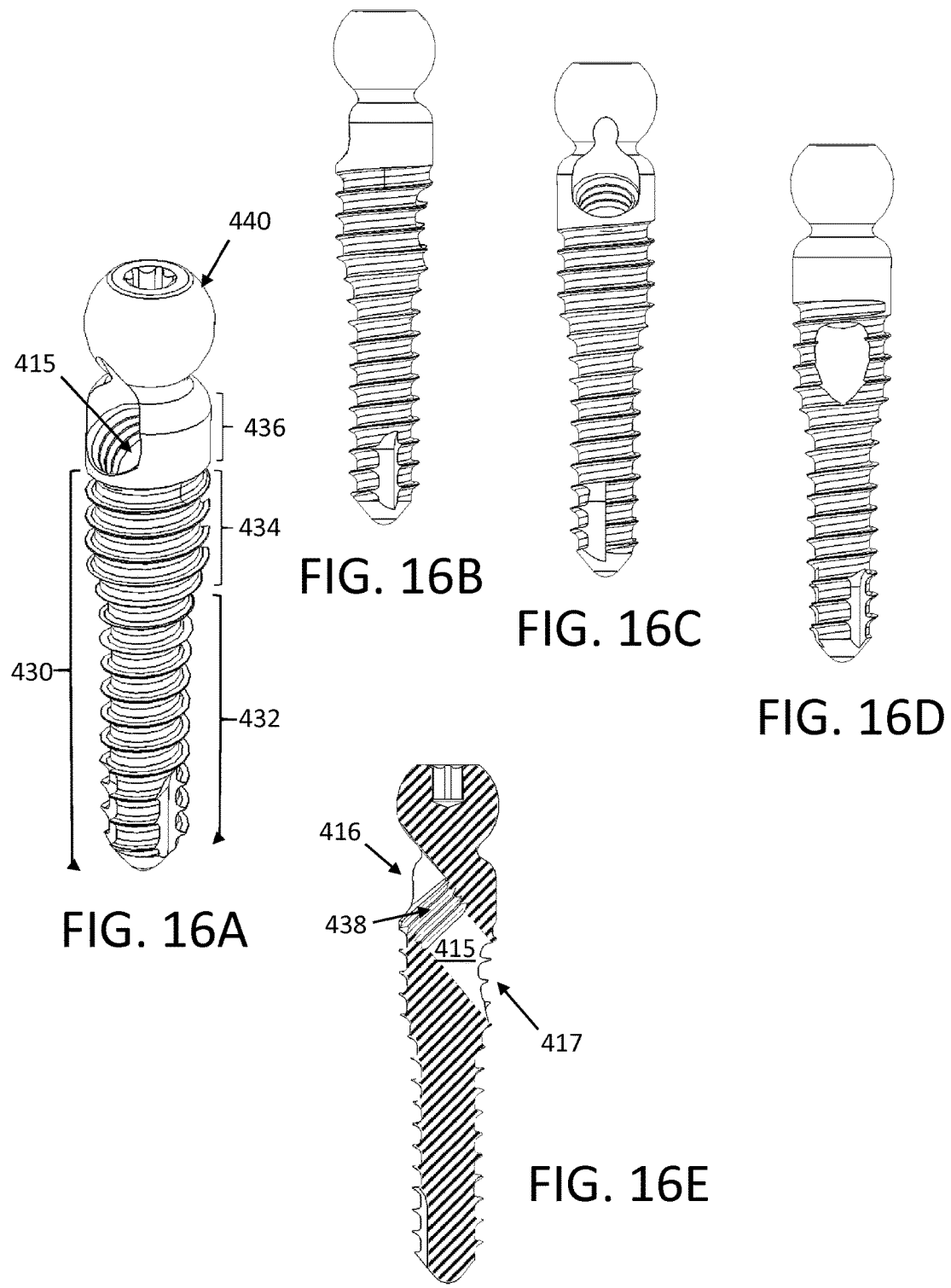
FIGS. 16A through 16E depict various views of a primary fixation screw which incorporates various features of the present invention.

As best seen in the cross-sectional view of FIG. 16E, the primary fixation screw 410 further includes a screw opening 415 formed in the shank 430, which in the depicted embodiment extends primarily from an upper opening 416 formed in the unthreaded section 436 of the screw, and extending through the proximal shank section 434 and exiting a lower opening 417 formed at a lower end of the proximal shank section 434. An interior surface of the screw opening 415 includes an internally threaded portion 438, which desirably mates with a corresponding proximal threaded portion 422 of the supplemental fixation screw 420.

While the opening 415 is depicted as being formed at an approximately 45 degree angle from a longitudinal axis of the primary fixation screw 410, openings with other angles could be utilized in alternative embodiments, including 60 degree holes, 55 degree holes, 50 degree holes, 40 degree holes, 35 degree holes, 30 degree holes and/or other angles. If desired, a kit having a plurality of primary fixation screws with differing opening angles could be provided, with a surgeon desirably choosing a fixation screw construct appropriate to the targeted anatomy of the patient.

Figure 17:
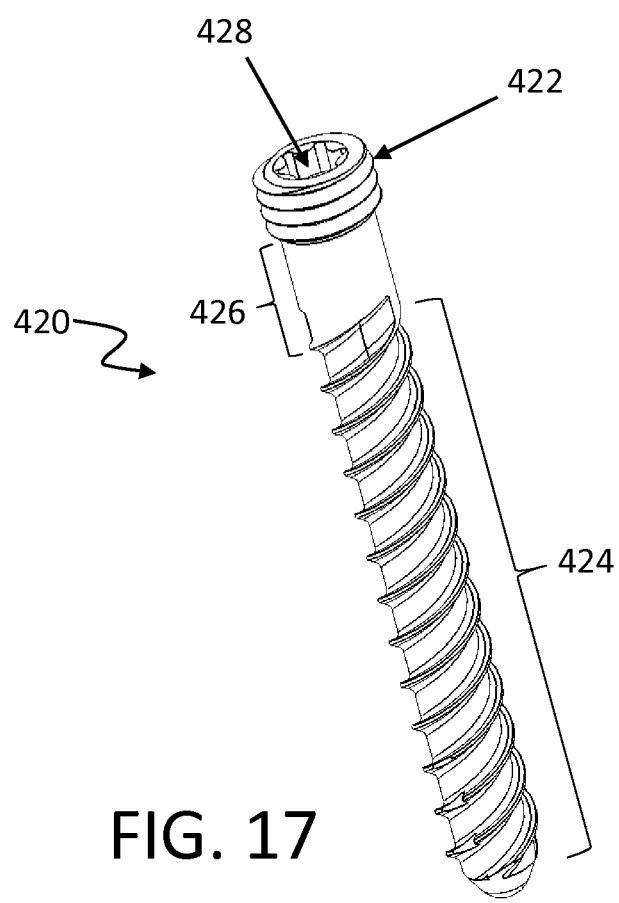
FIG. 17 depicts a perspective view of another embodiment of a supplemental fixation screw which incorporates various features of the present invention.

FIG. 17 depicts a perspective view of one embodiment of a supplemental fixation screw 420, which includes a proximal threaded section 422 and a distal threaded portion 424, with machine-type threads in the proximal threaded section and bony anatomy-engaging threads in the distal threaded portion (i.e., cortical and/or cancellous bone engaging threads, for example) in this embodiment. A hexalobe socket 428 is desirably formed in the proximal threaded section 422, which can be engaged with a corresponding surgical driver for advancement of the supplemental fixation screw 420 through the screw opening 415 and into the desired bony anatomy of the patient.

In use, a surgeon can initially place the primary fixation screw 400 and assembled insert 480 and tulip head 460 (which can be provided as a pre-assembled construct) into a targeted spinal anatomy of the patient, including the use of various preparation and placement tools known in the art for placement of pedicle screws. Desirably, a driving tool (not shown) can extend through an opening in the insert, with its tip extending into the hexalobe socket of the primary fixation screw, and the primary fixation screw advanced into the bone, which can include advancement of the primary fixation screw to a depth in the bone where the lower opening 417 is positioned below the surface of the bone while the upper opening 416 is at least partially exposed above the surface of the bone. (Other alternative embodiments could include advancement of the screw such that both openings extend at least partially below the bone surface, or where both openings are at least partially exposed above the bone surface, etc.) If desired, the surgeon can then prepare the supplemental anatomy for the supplemental fixation screw (i.e., by drilling and/or broaching, if desired), which might include rotating the primary fixation screw to realign the opening towards a desired location of the supplemental anatomy. Once the supplemental anatomy has been prepared, a supplemental fixation screw 420 can be introduced through the screw opening 415 and secured to the supplemental anatomy, with rotation of the supplemental fixation screw also desirably securing the supplemental fixation screw into the corresponding threads of the opening 415, as previously described. Once the screw fixation has been accomplished, the tulip head 460 can be freely realigned, and a fixation rod or other structure can be placed into the slot and the set screw 490 tightened into the tulip head 460, thereby locking and immobilizing the construct in a desired manner.

While many of the disclosed embodiments are specifically described in conjunction with sacral fixation, it should be understood that features of the present invention could be employed with equal utility in anatomical locations other than sacral levels that might benefit from the various supplemental fixation systems described herein. For example, a supplemental fixation construct could be utilized in a lumbar or other spinal level, with the primary fixation screw implanted into a pedicle of the vertebral body and the supplemental fixation screw implanted into the superior facet, if desired. Similarly, other anatomical locations of the body, including various joint structures, might benefit from the various supplemental fixation systems described herein.

By conforming to the patient's anatomy, spinal stabilization systems according to the present disclosure may provide better support and immobilization of the spine, and thus may accelerate the healing or fusion processes. This can represent a significant improvement over typical implant components, where a surgeon generally forms elongated members to conform to a patient's anatomy.

In the various embodiments described herein, the various mating surfaces and/or articulating connections could include a variety of frictional and/or engaging features, such as texturing on one or more of the mating surfaces, as well as the use of splines or serrated surfaces between such surfaces. The employment of texturing or other "roughening" of such mating surfaces can significantly increase the strength of the "locked" connections between such surfaces when the various components are tightened, and thereby desirably reduce the opportunity for slippage and/or failure of the one or more linkages under use. For example, in the disclosed system, the various components may include surface texturing of one or more of the engaging surfaces between the tulip head and a screw and/or between any of two or more surfaces that desirably engage when the construct is fully tightened.

In conjunction with the various stabilization system components described herein, various surgical instruments may be used in a spinal surgical procedure, including open, partially-open and/or minimally invasive procedures to implant and/or form a spinal stabilization system in a patient. Such instruments can include, but are not limited to, positioning needles, guide wires, dilators, bone awls, bone taps, sleeves, drivers, tissue wedges, trialing and length estimating tools, mallets, tissue retractors, positioning tools and tissue dilators. The instruments may be provided in an instrumentation set. The instrumentation set may also include components of the spinal fixation system. The components of the spinal fixation system may include, but are not limited to, bone fastener assemblies of various sizes and/or lengths, elongated members, and closure members.

The various components of the spinal stabilization systems and surgical instruments described herein may be made of a variety of materials including, but not limited to, titanium, titanium alloys, stainless steel, ceramics, and/or polymers. Some components of a spinal stabilization system may be autoclaved and/or chemically sterilized, while others may comprise sterile materials.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of implanting a surgical screw assembly, comprising:
   inserting a first shank of a first fixation component through a first opening in a central body, the first opening sized to accommodate the first shank, the first opening having a smaller diameter than a generally spherical head of the first fixation component;
   connecting the first shank of the first fixation component to a first location of a patient's spine;
   inserting a second fixation component through a second opening in the central body, the second opening sized to accommodate a second shank of the second fixation component, the second opening including an internally threaded portion for engaging with an externally threaded portion of the second shank;
   connecting the second shank of the second fixation component to a second location of the patient's spine;
   wherein the central body further includes an insert having an upper surface for accommodating a connecting rod, the insert comprising a central opening that aligns with the first opening and a first cutaway section that aligns with the second opening,
   wherein a first longitudinal axis of the first fixation component is not parallel to a second longitudinal axis of the second fixation component.

2. The method of claim 1, wherein the first fixation component is polyaxially adjustable relative to the central body.

3. The method of claim 1, wherein the first fixation component is monoaxially adjustable relative to the central body.

4. The method of claim 1, further comprising the step of accessing the second location of the patient's spine through the second opening to create a bone channel for accommodating the second fixation component.

5. The method of claim 1, wherein the first fixation element comprises a sacral screw and the second fixation element comprises an alar screw.

6. The method of claim 1, further comprising a screw for placement at least partially within an internal bore of the central body, the screw having an external thread form adapted for engagement with an internal surface of the central body, the screw having a top surface with a recess formed therein, the recess including a driver engagement portion formed into a plurality of walls of the recess for engaging a driving tool, the recess further including a threaded section formed into the plurality of walls of the recess, the threaded section at least partially overlapping the driver engagement portion.

7. The method of claim 1, further comprising placing a spinal rod into an upwardly extending slot of the central body.

8. The method of claim 1, wherein the central body comprises an internal bore, and the first and second longitudinal axes cross within the internal bore.

9. A bone anchor assembly, comprising
   a first fixation element configured to couple to a bone, the first fixation element having a first shank portion and a first head portion, the first shank portion having a first external thread form for engaging a bone;
   a housing portion having a lower opening for accommodating the first shank portion, the lower opening having a diameter smaller than a first outer diameter of the first head portion, the housing portion further including an internal bore and a first sidewall and a second sidewall forming a channel adapted to receive a connecting rod, at least a first portion of each sidewall including an internally facing thread form, the housing portion further including a second opening, the second opening extending through at least a second portion of one of the first and second sidewalls, the second opening adapted to accommodate a second fixation element, the second fixation element having a second external thread form for engaging the bone; and an insert for placement within the bore of the housing portion, the insert having an upper surface for accommodating the connecting rod, a central opening and a first cutaway section, wherein the central opening aligns with the lower opening of the housing portion and the first cutaway section aligns with the second opening in the housing portion.

10. The bone anchor assembly of claim 9, wherein the insert further comprises a generally spherical lower surface.

11. The bone anchor assembly of claim 9, wherein the first fixation element is polyaxially adjustable relative to the housing portion.

12. The bone anchor assembly of claim 9, wherein the second opening comprises a generally cylindrical bore, the generally cylindrical bore having a longitudinal axis of 30 to 45 degrees relative to a longitudinal axis of the internal bore of the housing portion.

13. The bone anchor assembly of claim 9, wherein the second opening is internally threaded.

14. The bone anchor assembly of claim 9, wherein the housing portion further comprises a third opening, the second opening extending through the second portion of the first sidewall and the third opening extending through the second portion of the second sidewall, the third opening adapted to accommodate a third fixation element, the third fixation element having a third external thread form for engaging the bone.

15. The bone anchor assembly of claim 14, wherein the insert further comprises a second cutaway section, wherein the second cutaway section aligns with the third opening in the housing portion.

16. The bone anchor assembly of claim 9, further comprising a screw for placement at least partially within the internal bore of the housing portion, the screw having a lower surface for engaging an outer surface of the connecting rod and an external thread form adapted for engagement with the internally facing thread forms of the first and second sidewalls, wherein tightening of the screw within the housing compresses the connecting road and insert, thereby locking the first fixation element relative to the housing portion.

17. The bone anchor assembly of claim 16, wherein the screw further includes a top surface with a recess formed therein, the recess including a driver engagement portion formed into the walls of the recess for engaging a driving tool, the recess further including a threaded section formed into the walls of the recess.

18. The bone anchor assembly of claim 17, wherein the threaded section of the recess at least partially overlaps the driver engagement portion of the recess.

19. The bone anchor assembly of claim 9, wherein an outer surface of the second fixation element engages with an inner surface of the second opening to lock the second fixation element relative to the housing portion.

20. The bone anchor assembly of claim 19, wherein at least a portion of the outer surface of the second fixation element includes an externally threaded portion that engages with an internally threaded portion of the second opening.

* * * * *